United States Patent
Dreyfus et al.

(10) Patent No.: US 12,213,655 B2
(45) Date of Patent: Feb. 4, 2025

(54) SUPPORT FOR A BIOLOGICAL SPECIES SAMPLE

(71) Applicants: UNIVERSITE GRENOBLE ALPES, Saint Martin d'Heres (FR); CENTRE HOSPITALIER UNIVERSITAIRE de GRENOBLE, La Tronche (FR); MEDIMPRINT, La Tronche (FR)

(72) Inventors: Matthieu Dreyfus, Grenoble (FR); Philippe Rossignolo, Echirolles (FR); Affif Zaccaria, Grenoble (FR)

(73) Assignees: UNIVERSITE GRENOBLE ALPES, Saint Martin d'Heres (FR); CENTRE HOSPITALIER UNIVERSITAIRE DE GRENOBLE, La Tronche (FR); MEDIMPRINT, La Tronche (FR)

( * ) Notice: Subject to any disclaimer, the term of this patent is extended or adjusted under 35 U.S.C. 154(b) by 1232 days.

(21) Appl. No.: 16/491,862

(22) PCT Filed: Mar. 7, 2018

(86) PCT No.: PCT/FR2018/050523
§ 371 (c)(1),
(2) Date: Mar. 22, 2021

(87) PCT Pub. No.: WO2018/162847
PCT Pub. Date: Sep. 13, 2018

(65) Prior Publication Data
US 2021/0239691 A1 Aug. 5, 2021

(30) Foreign Application Priority Data
Mar. 8, 2017 (FR) ...................................... 1751890

(51) Int. Cl.
*A61B 10/02* (2006.01)
*A61B 10/00* (2006.01)
(Continued)

(52) U.S. Cl.
CPC .......... *A61B 10/02* (2013.01); *A61B 10/0096* (2013.01); *B01L 3/505* (2013.01);
(Continued)

(58) Field of Classification Search
None
See application file for complete search history.

(56) References Cited

U.S. PATENT DOCUMENTS

2001/0026942 A1* 10/2001 Carpenter .......... A61B 10/0096
436/17
2005/0220677 A1 10/2005 Sangha
(Continued)

FOREIGN PATENT DOCUMENTS

FR 2955024 A1 * 7/2011 ......... A61B 10/0045
FR 2 999 872 6/2014
(Continued)

OTHER PUBLICATIONS

English machine translation of WO 2014096138 A1. Retrieved Mar. 21, 2024. (Year: 2024).*
(Continued)

*Primary Examiner* — Meredith Weare
(74) *Attorney, Agent, or Firm* — HAUPTMAN HAM, LLP (57) ABSTRACT

A support for a biological species sample collected on a sampling device including a gripping rod and a capture element having a capture surface for receiving the sample. The capture element being assembled with the gripping rod in order to form a distal portion of the sampling device. The support has a flat main face delimited by at least one side and a recess opening on the side of the support in which the sampling device can be inserted. The recess has a groove formed on the main face of the support in order to receive the distal portion of the sampling device. The groove being
(Continued)

configured to interact with the distal portion in order to securely hold it on or in the support.

16 Claims, 5 Drawing Sheets

(51) Int. Cl.
 *B01L 3/00* (2006.01)
 *G01N 33/543* (2006.01)
(52) U.S. Cl.
 CPC ............. *B01L 3/508* (2013.01); *B01L 3/5085* (2013.01); *B01L 3/52* (2013.01); *G01N 33/54386* (2013.01); *B01L 2300/0809* (2013.01); *B01L 2300/0887* (2013.01)

(56) References Cited

U.S. PATENT DOCUMENTS

| | | | |
|---|---|---|---|
| 2007/0207554 A1 | 9/2007 | Lin et al. | |
| 2009/0280523 A1* | 11/2009 | Benabid | A61B 10/02 435/29 |
| 2013/0079663 A1* | 3/2013 | Caillat | A61B 10/0045 600/562 |
| 2014/0377148 A1* | 12/2014 | Pasternak | G01N 33/4833 422/561 |
| 2014/0377793 A1* | 12/2014 | Bouamrani | G01N 33/543 600/562 |
| 2016/0296215 A1* | 10/2016 | Bouamrani | A61B 10/04 |

FOREIGN PATENT DOCUMENTS

| | | | | |
|---|---|---|---|---|
| FR | 3007634 A1 * | 1/2015 | ............. | A61B 10/02 |
| WO | WO-2006090220 A2 * | 8/2006 | ............. | A61B 10/02 |
| WO | WO 2013/105095 | 7/2013 | | |
| WO | WO-2013098703 A1 * | 7/2013 | ......... | A61B 10/0045 |
| WO | WO-2014096138 A1 * | 6/2014 | ......... | A61B 10/0096 |
| WO | WO 2014/141262 | 9/2014 | | |

OTHER PUBLICATIONS

International Search Report dated May 30, 2018 from corresponding application No. PCT/FR2018/050523.

* cited by examiner

SUPPORT FOR A BIOLOGICAL SPECIES SAMPLE

FIELD OF THE INVENTION

The present invention relates to a support for a biological species sample.

TECHNOLOGICAL BACKGROUND OF THE INVENTION

There are known from the prior art devices for sampling from a tissue or from a fluid, by merely placing in contact with a capture surface, a biological species sample with a view to the analysis thereof.

The biological species adsorbed on the capture surface may comprise cells, bacteria, viruses. Molecules, or macromolecules such as proteins or peptides may be involved. The dimensions of these biological species may be very variable, from the order of a nanometre to several tens of microns. The analyses conducted on the sample collected may be a confocal microscopy or MALDI (acronym of the term "Matrix-Assisted Laser Desorption/Ionisation") or SALDI (acronym of the term "Surface-Assisted Laser Desorption/Ionisation") laser desorption mass spectroscopy analysis. Biochemical, molecular biology polyomic (proteomic, transcriptomic and genomic, etc.) analyses are also possible. Storing and placing the sampled cells in culture may also be involved.

Figure 1:
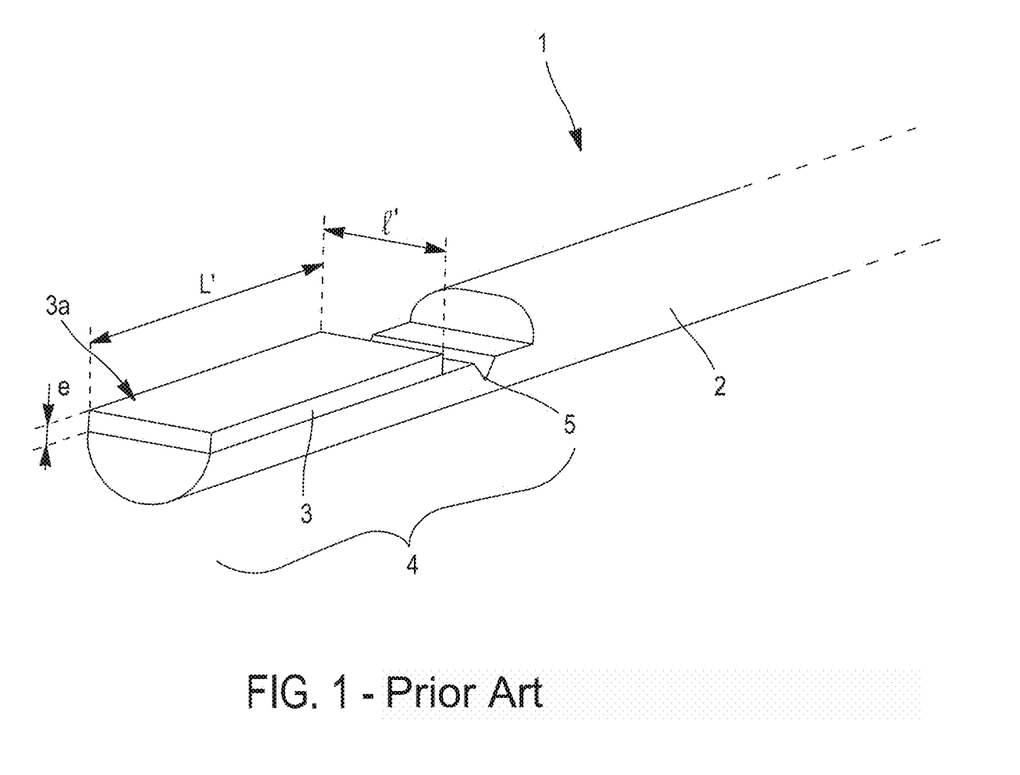
FIG. 1 represents a device for sampling a biological species sample according to the prior art.

There is represented in FIG. 1 such a device for sampling biological species, known for example from the documents WO2013/098703, FR2955024, WO2006/090220. The device 1 is formed of a gripping rod 2 and a biological species capture element 3. The capture element 3 is assembled with the gripping rod 2, for example by means of a biocompatible adhesive. The gripping rod 2 has a length suitable for the target application, i.e. for the insertion depth required to reach the tissues or organ for which analysis is sought. This length may be for example of the order of 20 cm. The rod also has a cross-section wherein the greatest dimension is relatively narrow, of the order of a millimetre or less than 1 mm. The free surface of the capture element 3 forms the capture surface 3a which receives the sample collected.

The capture surface 3a is a structured and/or functionalised surface encouraging the adsorption of the biological species when this surface is placed in contact with the tissues or fluid for which analysis is sought. The capture element 3 and surface 3a may be made of silicon, a capture element 3 may thus be a silicon chip. The capture element has a length "L" which may extend over several centimetres, a width "l" of the order of a mm, and a thickness "e" of some tenths of a mm, as well as that indicated in FIG. 1. The gripping rod 2 may be provided with a plurality of capture elements 3, for example juxtaposed in relation to one another along the length of the rod 2.

There will be denoted in the present application by the term "distal portion" 4, the end of the gripping rod 2 comprising the assembly of the capture element 3 and of this rod.

The gripping rod 2 may be provided with a mechanical breaking piece 5 or another mechanism for separating the distal portion 4 from the rest of the rod 2. Indeed, the latter is cumbersome and could impede handling, processing of the sample or the positioning thereof in analytical equipment.

After sampling, and in order to facilitate the handling of the sample collected, the capture element 3 or the distal portion 4 of the device 1 is generally disposed on a support. This support may be suitable for storing the sample or for preparing same for analysis.

There is known from the document FR3007634 a support suitable for receiving a biological species sample collected using a device according to that described above. This support is formed of a body having a planar surface whereon a plurality of slots have been formed. The slots have dimensions suitable for receiving the distal portion 4 of the sampling device and exposing the capture surface 3 so as to enable the analysis of the sample by analytical equipment.

The use of such a support has limitations, however. It requires prior separation of the distal portion 4 from the device 1 in order to subsequently place said portion manually into the slot thereof. This procedure is not easy to carry out, without risking damaging or contaminating the sample.

Furthermore, once placed in the slot thereof, the distal portion 4 is not held fixedly on the support. It is therefore liable to be dislodged therefrom, for example when moving the support to the analytical equipment. This drawback is all the more pronounced when the support is designed to receive a plurality of capture elements 3.

There is known also from the document WO 2006/090220 a support having, on one of the sides thereof, a longitudinal recess for inserting into the support the distal portion 4 of the sampling device 1. The recess wherein the sample is placed communicates with the surface of the support via channels opening onto this surface. This support makes it possible to place the capture surface 3a buried in the support in contact with a liquid with a view to separating and sampling the biological species from the capture surface 3a. When the distal portion 4a of the sampling device 1 is inserted into the support, the capture surface is not exposed to the surface of the support, which is not suitable for carrying out microscopy or spectroscopy type analyses.

There is also known from the document US2007207554 a support having, on one of the sides thereof, a longitudinal recess for inserting a test strip into the support. In this document, the recess communicates directly with the surface and comprises on the lower part thereof, a transparent part suitable for carrying out refractometry analyses by passing light through the sample.

The aim of the invention is that of remedying all or some of the drawbacks mentioned above. It is particularly intended to propose a support for a biological species sample that is easy to use, suitable for fixedly holding the capture element supporting the sample and carrying the analysis and/or processing thereof.

BRIEF DESCRIPTION OF THE INVENTION

With a view to achieving at least one of these aims, the subject of the invention proposes a support for a biological species sample collected on a sampling device comprising:
 a gripping rod;
 a capture element having a capture surface for receiving the sample, the capture element being assembled with the gripping rod in order to form a distal portion of the sampling device.

The support has a flat main face delimited by at least one side and a recess opening on the side of the support wherein the sampling device can be inserted, the recess consisting of a groove formed on the main face of the support in order to receive the distal portion of the sampling device, the groove being configured to interact with the distal portion in order to fixedly hold it on or in the support.

According to the invention, the support comprises a member for attaching a wall on the main face thereof to form a reservoir above at least a portion of the groove.

According to further advantageous and non-limiting features of the invention, taken alone or according to any technically feasible combination:
- the groove has a width measured at the level of the main face of the support strictly less than the maximum width thereof according to the depth thereof so as to hold the distal portion of the sampling device on or in the support when the latter is lodged in the groove;
- the support has a plurality of grooves;
- the grooves are parallel with one another;
- the support consists of a transparent material;
- the support is provided on the main face thereof with a conductive layer;
- the support consists of a metallic plate;
- the depth of the groove is such that the capture surface is flush with the main face of the support when the distal portion of the sampling device is lodged in the groove;
- the dimensions of the groove are adjusted to the dimensions of the distal portion to form a tight connection;

According to a further aspect, the subject matter of the invention proposes a biological species sample processing kit comprising a support and a wall of a reservoir.

According to further advantageous and non-limiting features of this kit, taken alone or according to any technically feasible combination:
- the processing kit further comprises a removable cover of the reservoir;
- the wall of the reservoir is formed from an opaque material;
- the reservoir comprises a plurality of tight compartments;
- the wall of the reservoir comprises an internal notch in order to receive the end of a dispensing micropipette.

The subject matter of the invention also proposes a system for inserting a sampling device into a support, comprising:
- a first element for placing a support fixedly, in an assembly plane;
- a second element for placing a sampling device fixedly in the assembly plane, the first element and the second element being disposed in relation to one another such that the gripping rod is placed facing and aligned with the groove of the support;
- an actuation device for moving the first element to face the second element in order to move them closer to one another and lodge the distal portion of the sampling device in the groove.

The insertion system may comprise a cutting device in order to detach the distal portion from the rest of the gripping rod.

BRIEF DESCRIPTION OF THE DRAWINGS

Further features and advantages of the invention will emerge from the following detailed description of the invention with reference to the appended figures wherein.

DETAILED DESCRIPTION OF THE INVENTION

For the purposes of simplification of the description hereinafter, the same references are used for identical elements or those carrying out the same function in the prior art or in the various embodiments described of the method.

The invention relates to a support 6 for a biological species sample. The sample is collected on a capture surface 3a of a sampling device 1 as described in the introduction of the application and an example of embodiment whereof has already been shown in FIG. 1. As a reminder, it is recalled nonetheless that the device 1 comprises a gripping rod 2 and a biological species capture element 3 assembled at one end of the rod 2. This assembly forms a distal portion 4 of the sampling device 1. This distal portion 4 may be breakable or detachable. The gripping rod may therefore provide a breaking zone 5, as represented in FIG. 1, or more generally, a member 5 for detaching the distal portion 4 from the rest of the device 1.

Figure 2A:
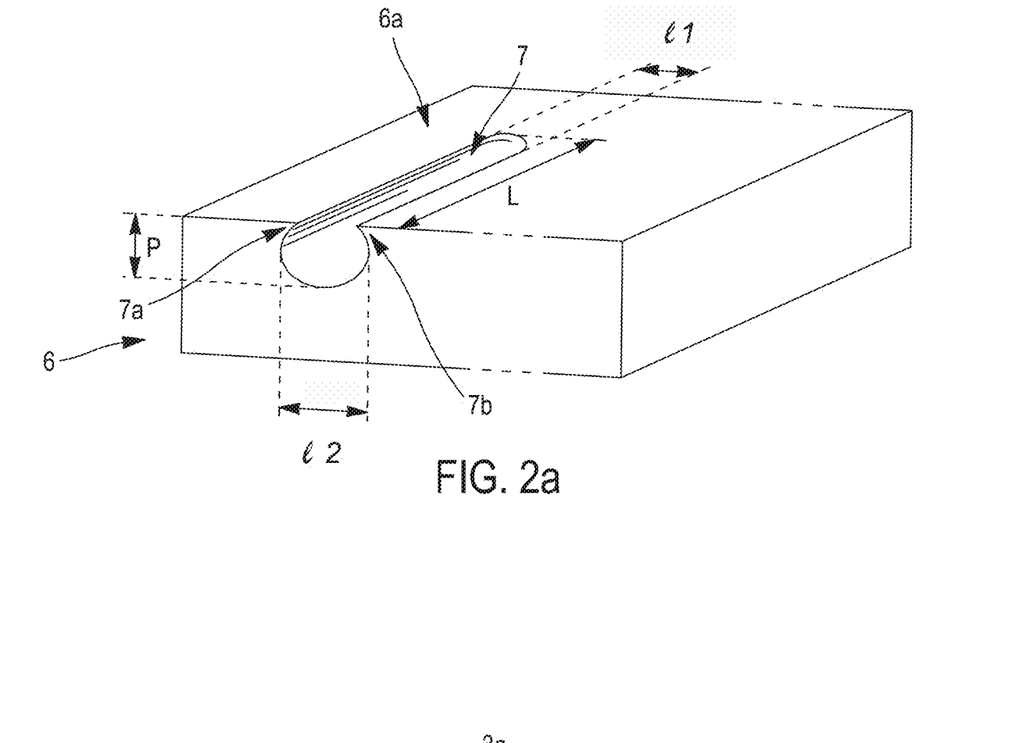
FIGS. 2a and 2b represent a support according to the invention.
Figure 2B:
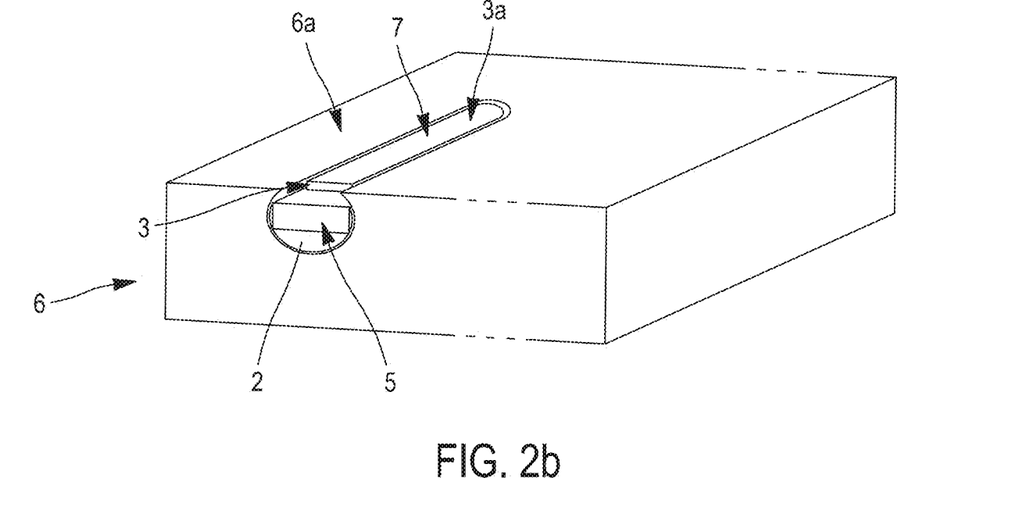

FIG. 2a represents a support 6 according to the invention. The support 6 has a flat main face 6a, delimited by at least one side or an edge. In the example in FIG. 2, the support 6 is of parallelepipedal shape, and therefore has four lateral edges forming the sides of the main face 6a. The invention is, however, not limited to this shape, and the support may have any number of lateral edges, defining the main face 6a.

The support 6 has a recess opening onto the side of the support wherein the end of the capture device 1 can be inserted. According to the invention, this recess consists of a groove 7 formed on the main face 6a of the support 6, and extending up to the side delimiting this main face 6a. When the distal portion 4 of the sampling device is suitably placed in the groove 7, the capture surface 3 is exposed at the level of the main face 6a of the support 6, as is clearly visible in FIG. 2b.

According to the invention, the groove 7 is configured to interact with the distal portion 4 of the sampling device 1 in order to hold it fixedly on or in the support 6, i.e. the distal portion 4 cannot come out of the groove 7.

In other words, the groove 7 includes a protruding portion 7a, 7b with which the distal portion 4 of the device is suitable for coming into contact so that it cannot come out of the groove 7.

Particularly advantageously, the protruding portion 7a, 7b also locks the rotational movement of the distal portion 4 in the groove 7, about the axis formed by the gripping rod 2 or the remaining portion of this rod 2. It is thus ensured that the capture surface 3a remains parallel or coplanar with the main face 6a of the support 6, which contributes to the quality of the analysis.

As a general rule, the shape and the dimensions of the groove 7 are chosen to match the shape and dimensions of the distal portion 4 of the sampling device 1 in order to hold it fixedly on or in the support 6. These dimensions must be sufficiently great to be able to insert therein the distal portion 4 of the device 1, by inserting same into the groove 7. These dimensions must be at the same time sufficiently adjusted so that the distal portion 4 is held fixedly in the groove 7.

Figure 2C:
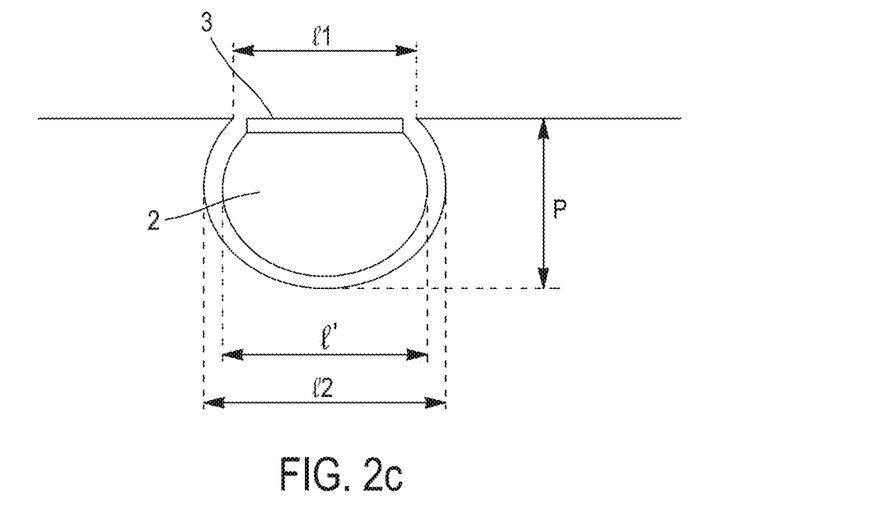
FIGS. 2c and 2d represent two examples of a cross-section of the support along an axis perpendicular to the groove, showing the cross-section of a groove of a support according to the invention.
Figure 2D:
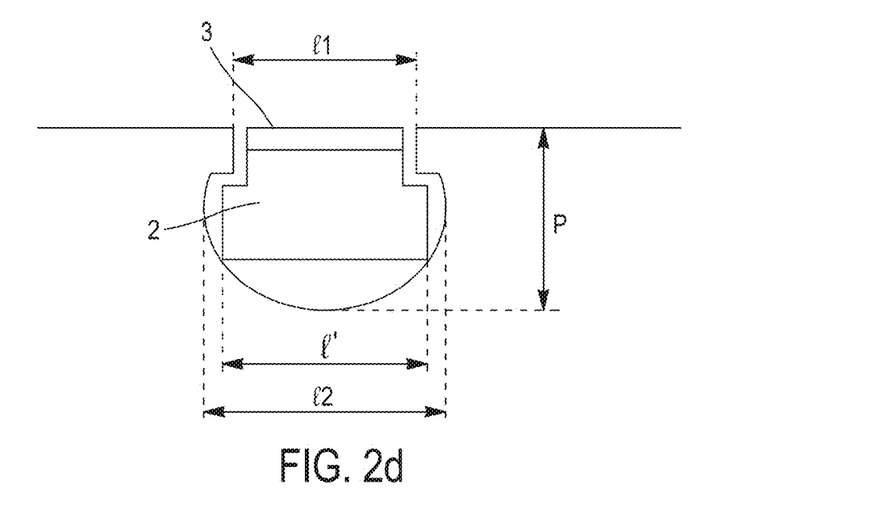

Multiple configurations are possible to ensure sufficient securing on or in the support 6, and FIGS. 2c and 2d represent, by way of illustration, two particular examples of a groove 7 and device 1 according to the invention. These figures are cross-sectional views of the support 7 along a plane perpendicular to the groove 7. These figures bear the length L, the depth P and the width 11, 12 of the groove 7.

In these two examples, the groove 7 has a width 11 measured at the level of the main face 6a of the support 6 strictly less than the maximum width 12 thereof according to the depth thereof. At the same time, the maximum width l' of the distal portion 4 is greater than the width 11 of the groove measured at the level of the main surface 6a. In this way, when the distal portion 4 of the device 1 is lodged in the groove 7, it is held fixedly in the groove 7 and cannot come out thereof.

In the two examples represented, the disk generated by the rotation of the cross-section of the distal portion, along an axis defined by the length of the rod has a greater dimension than the cross-section of the groove. Consequently, the rotational movement of the distal portion 4 along this axis of rotation is indeed locked.

Returning to the description of FIGS. 2a and 2b, the length L of the groove 7 is, preferably, greater than the length L' of the capture element 3. Thus, when the distal portion 4 is placed in the stop position in the groove 7, the capture element 2 is entirely lodged in the groove &, i.e. it does not protrude from the support 6. Very advantageously, the length L of the groove 7 matches or is slightly less than the distance separating the end of the gripping rod 2, in the stop position in the groove, and the mechanical breaking piece 5 or the disassembly member 5 of the distal portion 4 of the rod 2.

Once the device 1 has been inserted in the stop position in the groove 7, it is possible to break the gripping rod 2 at the level of the breaking piece 5 and detach the distal portion 4 thereof which then remains entirely lodged in the support 6. This break may be obtained by applying forces on the emerging portion of the gripping rod 2, these forces being, for example, possibly directed along a direction perpendicular to the main face 6a of the support 6.

Advantageously, and as is clearly visible in the cross-sectional views in FIGS. 2c and 2d, the depth p of the groove 7 is chosen such that the capture surface 2a is flush with the main face 6a of the support 6. This configuration ensures satisfactory precision of the analyses conducted on the sample, particularly when the latter correspond to confocal microscopy. The term "flush" denotes that the difference in level between the capture surface 3a and the main face 6a of the support 6 is less than 50 microns, or 20 microns, or 10 microns. Preferably, this difference in level is such that the capture surface 2a is positioned slightly below the main face 6a of the support 6, so as to prevent any risk of damage to the capture surface 2a.

In this embodiment, it is also particularly advantageous to have a groove 7 wherein the width 11 measured at the level of the main face 6a of the support 6 is just greater than the width l' of the capture surface. For example, the width 11 of the groove 7 may be greater by 10 microns than the width l' of the capture element 3. In this way, a liquid dispensed at the surface of the support 6 cannot flow readily in the gap existing between the flush capture surface 3a and the main face 6a of the support 6. There is formed in this way a tight connection between the support 6 and the distal portion 4a inserted into the groove 7. More generally, the dimensions of the groove 7 may be adjusted to the dimensions of the distal portion 4 to form a tight connection. This is particularly the case when the liquid has a viscosity similar to that of water.

Obviously, the support 6 has a sufficient thickness to be able to form therein the groove 7 without forming a zone liable to render the support mechanically weak. Thus, the support may have a thickness greater than 2 times or greater than 5 times the depth of the groove.

As a general rule, the support consists of a material or a plurality of materials which is not liable to retain the biological species in order to avoid contaminating the samples.

In some cases, and according to the needs of the analysis to be carried out on the sample, the support 6 may be chosen to consist of or comprise an electrically conductive material, or be coated with an electrically conductive film. In some cases also, the material of the support 6 may be transparent. In the case where a conductive film is placed on such a transparent support, this film may be chosen in indium-tin oxide (also known as the acronym ITO).

Thus, in a particular example of use, the support 6 takes the form of a strip of transparent material (for example glass or PMMA) the standardised dimensions whereof make it possible to place the support and the sample readily in the analytical equipment.

In a second particular example, the support 6 takes the form of a rectangular metallic plate, for example made of stainless steel, the dimensions whereof are chosen to be placed in an item of analytical, for example mass spectroscopy, equipment.

Advantageously, the support 6 is provided with a plurality of grooves 7, according to that described above. It is in this way possible to dispose on the same support 6 a plurality of samples. Preferentially, these grooves 7 are disposed parallel with one another so as to facilitate the sequencing of the analyses for each sample in the equipment, without having to handle the support 6 excessively.

Figure 3A:
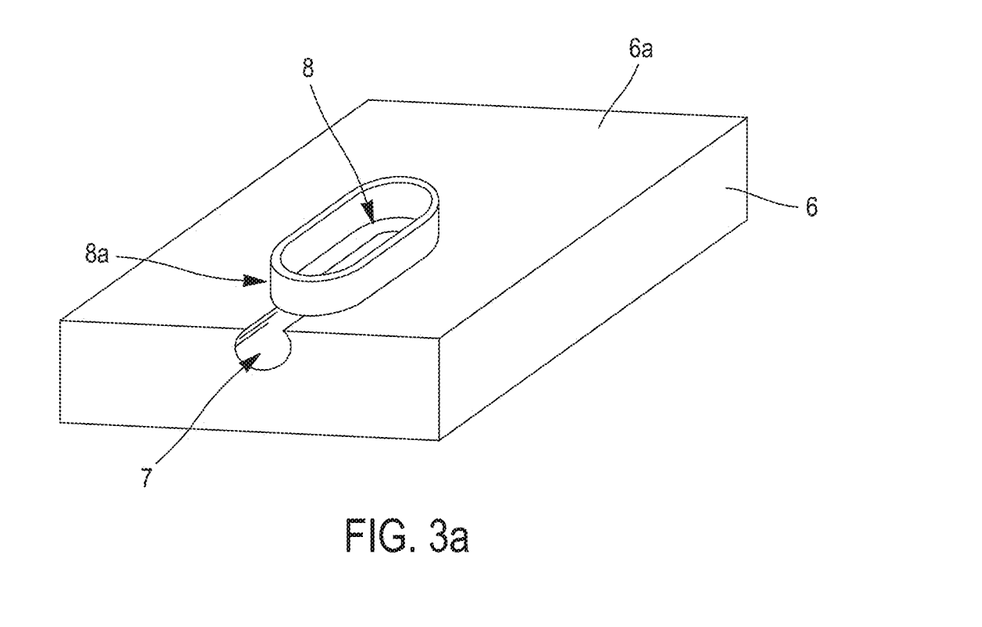
FIG. 3a represents a support provided with a liquid reservoir.

In the preferred embodiment of the invention, wherein the support 6 and the distal portion 4 form a tight connection, the support 6 may be provided with a reservoir 8, disposed above at least a portion of the groove 7, as represented in FIG. 3a. The reservoir may consist of or comprise a wall 8a having a closed contour. When the wall 8a is placed on the support 6, the main face 6a helps form the base of the reservoir 8. The reservoir 8 is envisaged to contain a liquid or a treatment solution such as a lysis buffer and place this liquid in contact with the sample.

The contour of the wall 8a may have a dimension, at the level of the face thereof in contact with the support 6, corresponding to the dimension (in width and/or in length) of the groove 7. It is therefore possible to place the sample and the liquid of the reservoir 8 in contact, while limiting the quantity of liquid contained in the reservoir 8. When recovering in the liquid, the biological species of the sample absorbed on the capture surface 3a, the small volume of the reservoir 8 ensures a high concentration of these species, which is particularly advantageous.

Figure 3B:
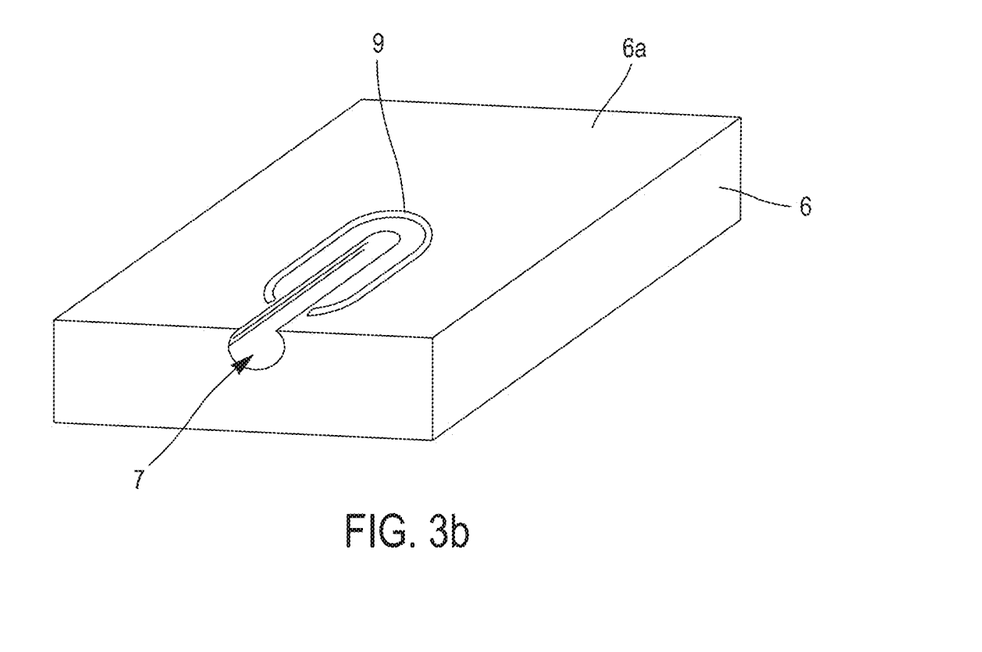
FIG. 3b represents a support according to the invention including a notch for placing a wall of a reservoir.

To be able to dispose the wall 8a fixedly and tightly on the support 6, the latter may be provided with a suitable attachment member. For example, and as represented schematically in FIG. 3b, the main face 6a of the support 6 may be provided with a peripheral notch 9 or a plurality of peripheral notches in relation to the groove 7 enabling the lower portion of the wall 8a of the reservoir 8 to be fitted removably.

The support 6 and the wall 8a of the reservoir 8 may be provided in a biological species sample processing kit, to enable a user to form the reservoir 8 as needed.

The wall 8a of the reservoir 8 may be opaque so that light does not affect the reactions or lack of reaction taking place between the liquid and the biological species. For the same reasons, the reservoir 8 may be provided with a cover or a lid which may also be opaque.

Like the support 6, the reservoir 8 is made of a material which does not retain or which is not liable to retain the biological species. It may for example consist of polyetheretherketone or polypropylene.

To facilitate dispensing of the liquid in the reservoir 8, the wall 8a may be provided at least with an internal notch designed to receive the end of the dispensing micropipette.

Figure 3C:
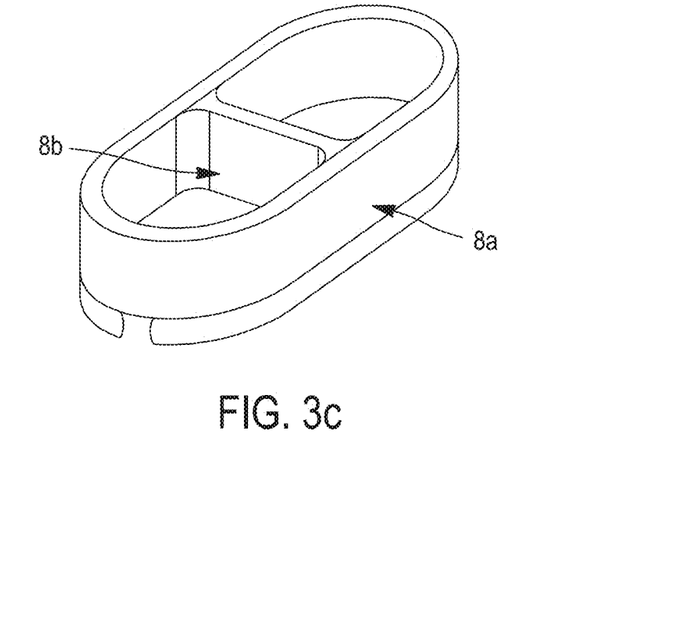
FIG. 3c represents a reservoir for a support according to the invention.

Advantageously, the reservoir 8 may comprise at least one internal wall 8b suitable for defining, inside the reservoir 8, a plurality of internal compartments mutually tight in relation to one another.

In this way, it is possible to process different sections of the capture surface 3a using liquids dispensed in each of the compartments. These liquids may be identical or different to one another. The different sections of the capture surface 3a may have been in contact with different types of tissues, and therefore bear samples of different types. It is possible by means of the compartmented reservoir 8 to process these sections simultaneously.

For example, and as represented in FIG. 3c, the internal walls 8b may be arranged along a direction essentially perpendicular to the groove 7, when the reservoir 8 is mounted on the support 6, in order to define compartments of the reservoir respectively overhanging a plurality of adjacent sections of the capture surface 3a, and successively disposed in the length of the groove 7.

According to a further example, the internal walls 8b of the reservoir 8 may be arranged along a direction essentially parallel with the groove 7 and define at least two compartments of the reservoir 8 respectively overhanging a plurality of adjacent sections of the capture surface 3a in the width of the groove. As in the preceding example, these two sections may be processed, simultaneously or not, and therefore additional sampling avoided.

Figure 4:
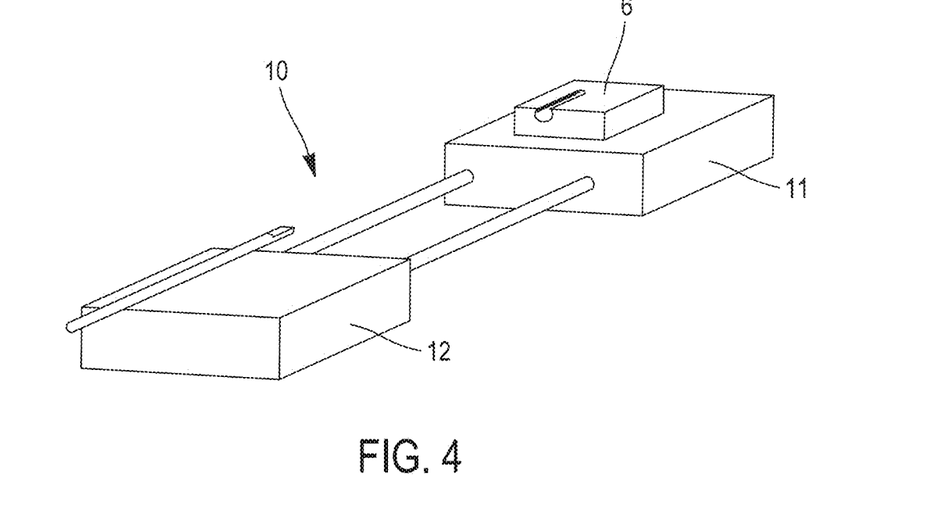
FIG. 4 represents a system for inserting a sampling device into a support according to the invention.

To facilitate the insertion of the sampling device 1 into the support 6 once sampling has been carried out, the invention also proposes a system 10 for inserting the sampling device 1 into the support 6. An example of such a system is represented in FIG. 4. The system comprises a first element 11 to hold the support 6 fixedly in an assembly plane. It also comprises a second element 12 for placing a sampling device 1 fixedly in the same assembly plane. The first element 11 and the second element 12 are disposed in relation to one another such that the gripping rod 2 is placed facing and aligned with the groove 7 of the support 6. The insertion system 10 also comprises an actuation device for moving the first 11 (and therefore the support 6) to face the second element 12 (and therefore the sampling device 1) to move them closer to one another and lodge the distal portion 4 of the sampling device 1 into the groove 7.

In FIG. 4, this insertion system 10 comprises two rails sliding in openings formed in the first element 11, but any other device for moving the first element 11 in translation to face the second element 12 with sufficient precision may be suitable.

The system 10 may also comprise a cutting or disassembly device, for example of the guillotine type, for detaching the distal portion 4 from the rest of the sampling device 1, for example at the level of the mechanical breaking piece 5 when such a piece has been formed on the gripping rod 2 of the sampling device.

Obviously, the invention is not restricted to the embodiments described and alternative embodiments may be added thereto without leaving the scope of the invention as defined by the claims.

Thus, although it has been envisaged to associate the support 6 with a reservoir 8, it is quite possible to associate this support 6 with a microfluidic system disposed on the surface of the support 6, and particularly overhanging the groove 7 so as, for example, to control with great precision the quantity of liquid or treatment solution placed in contact with the sample.

The invention claimed is:

1. A support for a biological species sample collected on a sampling device, the sampling device comprising:
   a gripping rod;
   a capture element having a capture surface for receiving the biological species sample, the capture element being assembled with the gripping rod in order to form a distal portion of the sampling device;
   wherein the support comprises:
      a flat main face delimited by at least one side of the support;
      a recess formed in the support, the recess consisting of a groove formed on the main face of the support that extends to an opening on a side of the support delimiting the main face thereof, wherein the groove is configured to: receive the distal portion of the sampling device via the opening, and interact with the distal portion of the sampling device in order to hold the distal portion of the sampling device in the support; and
      a member for attaching a wall on the main face of the support to form a reservoir above at least a portion of the groove.

2. The support according to claim 1, wherein the groove has a width measured at a level of the main face of the support strictly less than a maximum width of the groove so as to hold the distal portion of the sampling device in the support when the distal portion is lodged in the groove.

3. The support according to claim 1, wherein the support comprises a plurality of grooves each with a respective recess opening.

4. The support according to claim 3, wherein the plurality of grooves are parallel with one another.

5. The support according to claim 1, wherein the support is made of a transparent material.

6. The support according to claim 1, wherein the main face comprises a conductive layer.

7. The support according to claim 1, wherein the support is made of a metallic plate.

8. The support according to claim 1, wherein a depth of the groove is configured such that the capture surface is flush with the main face of the support when the distal portion of the sampling device is lodged in the groove.

9. The support according to claim 1, wherein dimensions of the groove are selected to cooperate with dimensions of the distal portion of the sampling device to form a tight connection.

10. A biological species sample processing kit comprising:
    the support according to claim 9; and
    a wall of a reservoir.

11. The biological species sample processing kit according to claim 10, further comprising a removable cover of the reservoir.

12. The biological species sample processing kit according to claim 10, wherein the wall of the reservoir is formed from an opaque material.

13. The biological species sample processing kit according to claim 10, wherein the reservoir comprises a plurality of watertight compartments.

14. The biological species sample processing kit according to claim 10, wherein the wall of the reservoir comprises an internal notch in order to receive an end of a dispensing micropipette.

15. An insertion system for inserting a sampling device into a support, comprising:
- the support according to claim 1;
- a first element for placing the support in an assembly plane; and
- a second element for placing the sampling device in the assembly plane, the first element and the second element being disposed in relation to one another such that the gripping rod is placed facing and aligned with the groove of the support,
- wherein the first element is configured to move toward the second element in order to lodge the distal portion of the sampling device in the groove.

16. The insertion system according to claim 15, further comprising a cutting device in order to detach the distal portion of the sampling device from a rest of the gripping rod.

\* \* \* \* \*